United States Patent [19]

Gosciniak

[11] Patent Number: 5,081,308
[45] Date of Patent: Jan. 14, 1992

[54] ULTRAVIOLET RADIATION ABSORBING COMPOSITIONS OF BIS-1,3-DIKETONE DERIVATIVES OF CYCLOHEXANE

[75] Inventor: Donald J. Gosciniak, West Chester, Pa.

[73] Assignee: ICI Americas Inc., Wilmington, Del.

[21] Appl. No.: 284,518

[22] Filed: Dec. 15, 1988

[51] Int. Cl.$^5$ ............................................ C07C 49/225
[52] U.S. Cl. .................................... 568/329; 424/59; 560/54; 558/415
[58] Field of Search .......................... 568/329; 424/59

[56] References Cited

U.S. PATENT DOCUMENTS

| | | | |
|---|---|---|---|
| 2,315,063 | 3/1943 | Lieber | 568/329 |
| 3,789,062 | 1/1974 | Idelson | 568/329 |
| 4,308,400 | 12/1981 | Felder et al. | 568/329 |
| 4,371,651 | 2/1983 | Leistner | 524/236 |
| 4,489,057 | 12/1984 | Welters et al. | 424/47 |

*Primary Examiner*—James H. Reamer
*Attorney, Agent, or Firm*—William E. Dickheiser

[57] ABSTRACT

Sunscreen compositions are described which contain certain bis-1,3-diketone derivatives of cyclohexane when incorporated in a carrier in amounts ranging from 0.1–50% by weight.

5 Claims, No Drawings

ULTRAVIOLET RADIATION ABSORBING COMPOSITIONS OF BIS-1,3-DIKETONE DERIVATIVES OF CYCLOHEXANE

The present invention is directed to ultraviolet absorbing compositions comprising certain conjugated bis-1,3-diketone derivatives of cyclohexane and blends thereof which are useful as protective coatings and to a method for protecting substrates against the harmful effects of actinic radiation. It is further directed to a process for making ultraviolet absorbing coating compositions.

Ultraviolet radiation absorbing coatings are useful in protecting substrates such as plastics against accelerated deterioration and the skin of warm blooded animals against severe erythema, edema and blistering when exposed to sunlight. The bis-diketone compositions of this invention are generally referred to as sunscreen compositions and blends thereof can be incorporated with waxes, oils, lacquers and soft resins in the preparation of furniture and auto polishes, as well as cosmetics, suntan oils, lotions, lipstick, hair treatments, skin formulations and in addition can be incorporated with contact lenses.

This invention relates to sunscreen compositions comprising a carrier having incorporated therein an effective amount of a ultraviolet absorber selected from a compound of general Formula I:

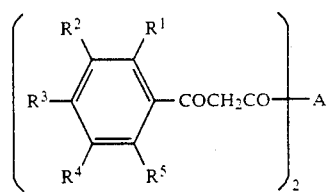

Wherein $R^1-R^5$ are independently selected from H, both linear and branched alkyl groups having from 1 to 10 carbon atoms, aryl, alkylaryl, $-OR^6$ where $R^6$ is an alkyl group having from 1-10 carbon atoms, halogen, $-CN$, $-NO_2$, $-NH_2$, $-NHR^7$ and $-N(R^7)_2$ wherein $R^7$ is an alkyl group of from 1 to 4 carbon atoms and $-CO_2R^8$ wherein $R^8$ is an alkyl group of from 1 to 10 carbon atoms; —A— is selected from a bivalent (1,2), (1,3) or (1,4) cyclohexylene radical having formula II, III or IV.

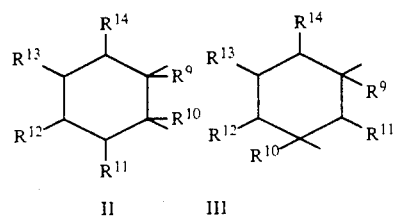

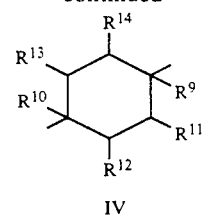

wherein $R^9$ and $R^{10}$ are independently selected from either H or $-CH_3$, $R^{11}-R^{14}$ are independently selected from H, alkyl groups having from 1 to 10 carbon atoms and $-OR^6$ wherein $R^6$ is as previously defined. Preferred compounds are those where $R^1-R^5$ and $R^9-R^{14}$ are hydrogen while A is 1,4-cyclohexylene and where $R^1$, $R^2$, $R^4$, $R^5$ and $R^9-R^{14}$ are hydrogen, $R^3$ is methoxy and A is 1,4-cyclohexylene.

The method for protecting substrates comprise optically applying the compound of formula I in an acceptable carrier. Of particular interest are compounds which provide selective absorption of UV radiation in the 290-320 nm as well as the 320-400 nm range of wave lengths. The compounds may be dissolved in the coating compositions or present as a finely divided solid or as a solid dispersed in an acceptable carrier. The selection of carrier used in the coating composition must not interfere with the absorption in the 290-400 nm range. In some instances interaction of the bis-diketone with a carrier shifts absorption outside the desired range and is not acceptable.

The compositions of the invention comprise UV filter compounds of Formula I in amounts needed to provide desired protection against the harmful effects of ultraviolet radiation. The concentration of the compounds in the composition is regulated such that when the composition is topically applied, the desired protection is provided. The amount needed to provide the desired protection can vary with the characteristics of the compound, that is, its extinction coefficient or substantively, the nature of the carrier, the source and intensity of the radiation and other well recognized variables. Suitable amounts can be readily determined by standard methods of testing. Preferably UV filter compounds are incorporated in an amount ranging from about 0.1 percent to about 50 percent by weight and usually in amounts of 1.0-30 percent by weight and preferred amounts ranging from 1.5-15 percent by weight based on the total weight of the coating composition.

Acceptable carriers include any vehicle or medium capable of incorporating the UV filter compound in a manner permitting uniform topical application. The term "pharmaceutically acceptable" is intended as a qualifier when the carrier is dermatologically innocuous to warm blooded animals and cosmetically acceptable. However all carriers are not useful on skin. The carrier may comprise a wax, oil or cream base material in which the agent can be held in a clear solution or a uniform dispersion for example as submicron sized particles. Preferably the carrier comprises a suitable solvent or a mixture of solvents capable of dissolving the UV filter compounds to provide a concentration that is effective as a filtering agent when incorporated in the sunscreen formulation. Solvents which may be useful include alcohols, ketones, esters, polyol esters, oils, hydrocarbons, chlorinated hydrocarbons, ethers, polyethers, polyether polyols and other special solvents such as dimethylsulfoxide, dimethylformamide, dimethylisosorbide, isopropylmyristate and the like. Such solvents are considered useful only if they do not permanently interact with the active UV filtering compound of the invention to shift the total effective absorption outside the 290–400 nm range. Some of the above named ingredients are not pharmaceutically acceptable but are useful in other applications.

The invention is directed to a method for protecting a substrate against the effects of ultraviolet radiation which comprises topically applying the above described compounds in a carrier.

The sunscreening compositions may be applied as a clear liquid or a lotion comprising a water-in-oil, oil-in-water or a multiple emulsion. Either the oil or water base or both may be used as a carrier for the sunscreening composition. The oil base material and the water and oil base compositions will form a continuous film of the UV filtering compound. Such films also provide long lasting protection against sun induced erythema. Sunscreening formulations are generally used in hot weather and at beaches where people enjoy bathing activity. It is also essential that the protective coating applied to the skin is not appreciably affected by water or perspiration. The pharmaceutically acceptable compositions herein disclosed are included in a thin layer protective coating on the skin of warm blooded animals and provide long lasting protection against erythema and do not appreciable decompose over practical periods of exposure to sunlight.

In general the compounds are synthesized by condensing the enolate of the corresponding ketone with a diester such as dimethyl 1,4-cylcohexanedicarboxylate in an inert solvent such as 1,2-diethyoxyethane or N,N-dimethylformamide.

The following compounds exemplify, but do not limit, the active compounds of the Formula I:

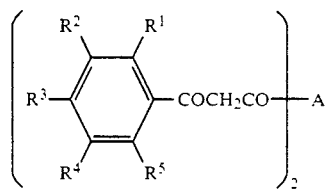

1,1'-(1,4-cyclohexylene)-bis-3-phenylpropane-1,3-dione.
1,1'-(1,4-cyclohexylene)-bis-4-methoxy-3-phenylpropane-1,3-dione.
1,1-(2,3-dimethoxy-1,4-cyclohexylene)-bis-3-phenylpropane-1,3-dione.
1,1'-(2,3,5,6-tetramethoxy-1,4-cyclohexylene)-bis-3-phenylpropane-1,3-dione.
1,1'-(2,3-dimethyl-1,4-cyclohexylene)-bis-3-phenylpropane-1,3-dione.
1,1'-(1,4-dimethyl-2,5-dimethoxy-1,4-cyclohexylene)-bis-3-phenylpropane-1,3-dione.
1,1'-(1,3-cyclohexylene)-bis-4-methoxy-3-phenylpropane-1,3-dione.
1,1'-(2-methylcarboxylate-1,4-cyclohexylene)-bis-3-phenylpropane-1,3-dione.
1,1'-(1,4-cyclohexylene)-bis-2,6-di-t-butyl-4-methoxy-3-phenylpropane-1,3-dione.
1,1'-(1,3-cyclohexylene)-bis-2,6-di-t-butyl-4-methoxy-3-phenylpropane-1,3-dione.
1,1'-(1,3-cylcohexylene)-bis-3-phenylpropane-1,3-dione.
1,1'-(1,2-cyclohexylene)-bis-3-phenylpropane-1,3-dione.
1,1'-(1,2-cyclohexylene)-bis-4-methoxy-3-phenylpropane-1,3-dione.

Compounds of the invention are best prepared by reaction of the enolate of the appropriately substituted acetophenone with the corresponding cyclohexylene diester. The substituted starting materials can be prepared by known methods such as that described by Chang et. al. (J. Org. Chem. 1976, 41, 335), Schreyer (Fr. Demande 2, 006, 477) and Matsuura (J. Org. Chem., 1962, 27, 3620). The following preparative examples serve as nonlimiting illustrations of the type of compounds included in the invention.

PREPARATION 1

Synthesis of 1,1'-(1,4-cyclohexylene)-bis-3-phenylpropane-1,3-dione.

In a 500 ml three-necked flask equipped with a mechanical stirrer, nitrogen inlet and addition funnel is placed dry 1,2-diethoxyethane (150 ml). To this is added sodium hydride (9.9g, .4mol) followed by dropwise addition of acetophenone (24g, 0.2mol) over a thirty minute period. Upon completion of the addition, the reaction is stirred an additional 15 minutes at room temperature. Dimethyl 1,4-cyclohexanedicarboxylate (20g, 0.1 mol) is added dropwise to the mixture. The reaction is then heated at 70° C. until complete. The reaction mix is then cooled to room temperature and poured into $H_2O$ (1L). The pH is adjusted to 4.5 with hydrochloric acid and the resulting precipitate is collected by filtration and washed with water. Upon drying, 32.6g of crude product (87%) is attained. Recrystallization results in pure material (mp = 165–167° C.) having a peak absorption of 315 nm; molar extinction coefficient = 32,164.

PREPARATION 2

Synthesis of 1,1'-(1,4-cyclohexylene)-bis-4-methoxy-3-phenylpropane-1,3-dione.

This material is prepared by repeating the procedure of preparation 1 substituting 4-methoxyacetophenone for acetophenone. The product has a peak absorption of 326 nm and a molar extinction coefficient of 41,644.

PREPARATION 3

Synthesis of 1,1'-(1,3-cyclohexylene)-bis-3-phenylpropane-1,3-dione.

This material is prepared by the procedure of preparation 1 substituting dimethyl 1,3-cyclohexane dicarboxylate for dimethyl 1,4-cyclohexane dicarboxylate.

PREPARATION 4

Synthesis of 1,1'-(1,3 cyclohexylene)-bis-4-methoxy-3-phenylpropane-1,3-dione.

This material is prepared by the procedure of preparation 1 using dimethyl 1,3-cyclohexane dicarboxylate and 4-methoxy acetophenone.

PREPARATION 5

Synthesis of dimethyl
(1,4-dimethyl-2,5-dihydroxy-1,4-cyclohexylene) dicarboxylate.

To a solution of 1,4-cyclohexane dicarboxylic acid, 2,3-dioxo-dimethyl ester (.01 mol) in methanol (20 ml) at 0° C. was added sodium borohydride (0.025 mol) portionwise over a fifteen minute period. The reaction was warmed to room temperature, quenched with water (20 ml) and extracted with ethyl acetate (2 ×25 ml). The organic fraction is separated, dried over anhydrous sodium sulfate, filtered and concentrated. Column chromatography (SiO$_2$) of the crude material leads to pure 1,4-cyclohexane dicarboxylic acid, 2,3-dihydroxy-dimethyl ester.

PREPARATION 6

Synthesis of dimethyl
(1,4-dimethyl-2,5-dimethoxy-1,4-cyclohexylene) dicarboxylate.

To a freshly prepared solution of lithium diisoproylamine (0.022 mol) in dry THF (25 ml) at −20° C. is added dropwise a solution of 1,4-cyclohexane dicarboxylic acid 2,3-dihydroxy-dimethyl ester (0.01 m) in THF. The solution is warmed to 0° C. and methyl iodide (0.04 m) is added dropwise. Upon completion the reaction is quenched with water (20 ml) and extracted with ethyl acetate (2×25 ml). The combined organic layer is dried over sodium sulfate, filtered and concentrated. Column chromatography (SiO$_2$) of the reaction crude yields the pure 1,4-cyclohexane dicarboxylic acid, 2,3-dialkoxy-dimethyl ester.

PREPARATION 7

Synthesis of dimethyl (1,4-dimethyl-1,4 cyclohexane) dicarboxylate.

To a refluxing solution of 1,4-dimethyl 1,4-cyclohexane dicarboxylic acid (0.01 m) in methanol is added dropwise a catalytic amount of Tyzor TBT (0.01 mmol). The reaction is held at reflux until completion, then cooled and water (25 ml) added. The reaction is then extracted with ethyl acetate (3×25 ml), the layer separated and the organic layer dried over anhydrous sodium sulfate, filtered and concentrated. Column chromatography of the crude material yields pure 1,4-cyclohexane dicarboxylic acid, 1,4-dimethyl ester.

PREPARATION 8

Synthesis of 4-methoxy-3,5-di-t-butyl acetophenone.

To a solution of 4-hydroxy-3,5-di-t-butyl acetophenone (0.01 m) and potassium carbonate (0.01 m) in acetone (50 ml) at 0° C. is added dropwise dimethyl sulfate (0.01 m) over 0.5 hr. period. The reaction is warmed to room temperature and stirred until completion. The reaction is then poured into water (100 ml) and the crude product is isolated and dried. Recrystallization yields pure 4-methoxy-3,5-di-t-butyl acetophenone.

It has been established that actinic radiation between 290nm and 320nm produces substantially all the burning or erythemal energy and a substantial portion of the tanning energy, while the radiation between 320nm and 400nm produces incident tanning. The cosmetic industry has divided these spectra into the burning range UV-B (290-320 nm) and the tanning range UV-A (320-400 nm). Since approximately 75% of the physiological tanning potential of sunlight is found in the UV-B range and the balance is found in the UV-A range, it is desirable to have a substantial amount of the radiation in those ranges filtered out before it produces a harmful effect on the surface of human skin. While sunscreen lotions have been formulated to be most effective in the UV-B range, recent studies have indicated that it is desirable to have collective adsorption in the UV-A range as well. It has been difficult to find a practical compound which effectively absorbs in both ranges. Therefore, formulators must resort to the combination of two compounds which are each effective either in the UV-B, or UV-A range to provide maximum skin protection. No single compound falling within the definition of formula I is effective over the entire 290-400 nm range and therefore two or more compounds can be selected and blended within the formulation at varying concentrations until the desired balance between burning and tanning is accommodated. Such a combination is shown in Example 13. It is preferred to have a formulation having at least one compound which absorbs in the 290-320 nm range and at least one other which absorbs in the 320-400 nm range. At least one is selected from Formula I.

The use of the UV filters of the invention can be demonstrated in lotion formulations which are topically applied to the surface of the skin. The effectiveness of the UV light absorbers are tested on human subjects by treating a 1 cm square section of a subjects' back with predetermined amounts of lotion, exposing the treated areas to UV light for a period of time and thereafter making a visual comparison with untreated and fully masked skin areas. The SPF (skin protection factor) is calculated by comparing the effects of radiation on protected skin with the unprotected skin.

Besides the SPF determinations on humans, many in vitro methods and in vivo tests on animal models are also widely used. Some of these methods yield results which correlate well with SPF determined on humans and are useful tools for evaluating new compounds.

The following lotions and creams will serve to illustrate but not limit those which can be used in the practice of the invention.

In general, typical formulating techniques are well known to skilled formulators and usually require that the filtering agent be first added to the oil phase which is thereafter emulsified. With regards to examples 1-2, all ingredients can be mixed together and stirred in conventional apparatus. Since in many cases a single compound used at a reasonable concentration does not effectively protect throughout the whole region of the earth reaching solar UV spectrum, blends of two or more UV absorbers can be used in a formulation to afford greater protection.

TABLE 1

| Ingredient | Examples (% by Weight) | |
|---|---|---|
| | (1) | (2) |
| (A) | | |
| Compound of Prep. 2 | 5 | 2 |
| Mineral oil (Carnation) | 5 | 5 |
| Stearyl alcohol | .5 | .5 |
| Cetyl alcohol | .5 | .5 |
| Silicone oil (SF-96, 350 cs) | .5 | .5 |
| Polyoxyethylene (21) stearyl ether | 2 | 2 |
| Polyoxyethylene (2) stearyl ether | 2 | 2 |
| (B) | | |
| Water (deionized) | 73.95 | 76.95 |
| Carbopol ® 934, (2% soln) | 10 | 10 |

TABLE 1-continued

| Ingredient | Examples (% by Weight) | |
|---|---|---|
|  | (1) | (2) |
| (C) Sodium hydroxide (10% aq.) | .2 | .2 |
| (D) DNDNH-55 (Glyco) | .35 | .35 |
| (E) Dimethyl isosorbide | 0 | 0 |

BLENDING PROCEDURE FOR EXAMPLES 1 AND 2

Blend ingredients A and heat to 70° C. In a separate container heat ingredients B to 75° C. and add to A. Add C to AB then cool to 40° C. Add ingredient D with stirring.

In addition to their use in coating skin surfaces to prevent sunburn the compositions of the invention can also be employed in various formulations such as waxes, oils, lacquers and soft resins in the preparation of furniture and auto polishes, cosmetics, lipstick, hair treatments, skin formulations and contact lenses. The compounds of the invention act as filtering agents and may be used singly or in combination to provide a wider range of protection. The following formulations are given to demonstrate a few of the many applications.

| Example No. | Filtering Agent | Carrier Ingredients | Composition (% by Wt) |
|---|---|---|---|
| 3 |  | Aerosol Hairdressing |  |
|  | Prep 2 |  | 5.0 |
|  |  | Decaglycerol monolaurate | 2.0 |
|  |  | Polypropylene (200) monooleate | 3.0 |
|  |  | Ethoxylated (10) lanolin alcohols | 1.0 |
|  |  | Propylene glycol | 2.0 |
|  |  | Ethyl alcohol, anhydrous | 39.5 |
|  |  | Protein polypeptide (20% alcoholic) | 1.2 |
|  |  | Isopropyl myristate | 1.3 |
|  |  | Propellant 11 | 15.0 |
|  |  | Propellant 12 | 30.0 |
|  |  | Water | q.s. |

Procedure for Formula: Dissolve all ingredients in slightly warmed ethyl alcohol, avoiding loss of the alcohol, add the water, and agitate well to disperse any haze. Filter the concentrate and fill into aerosol containers. Add propellants.

| Example No. | Filtering Agent | Carrier Ingredients | Composition (% by Wt) |
|---|---|---|---|
| 4 |  | Formula for Creamy Type Lipstick Base |  |
|  | Prep 2 |  | 5 |
|  |  | Carnauba wax | 3 |
|  |  | Candelilla wax | 7 |
|  |  | Ozokerite | 3 |
|  |  | Beeswax | 7 |
|  |  | Lanolin | 10 |
|  |  | Castor oil | 60 |
|  |  | Isopropyl myristate | 5 |
|  |  | Perfume | q.s. |
| 5 |  | Water-In-Oil (W/O), Detergent Resistant, Liquid Auto Polish |  |
|  | Part A | 2.00% Durmont 500 Montan Wax | (Dura Commodities) |
|  | Part B | 0.75% DC 530 Silicone Fluid | (Dow Corning) |
|  |  | 4.25% DC 531 Silicone Fluid |  |
|  |  | 1.50% SPAN ® 80 sorbitan monooleate | (ICI Americas) |
|  |  | 10.00% Kerosene |  |
|  |  | 16.50% Stoddard Solvent |  |
|  |  | 5.0% Preparation 2 |  |
|  | Part C | 10.00% Kaopolite TM SFO | (Kaopolite) |
|  | Part D | 50.00% Water |  |

Method of Preparation:
1. Melt wax in Part A (85-90° C.)
2. Add Part B ingredients to melted wax and stir to blend well. Return temperature to 85-90° C.
3. Add Part C to Part A/Part B blend and mix until uniform with medium agitation. Keep temperature in the 85-90° C. range.
4. Heat Part D to 95° C. and slowly add to the blend with high speed stirring until emulsion is obtained.
5. Cool to 40-45° C. with continuous stirring.
6. Homogenize.

| Example No. | Filtering Agent | Carrier Ingredients | Composition (% by Wt) |
|---|---|---|---|
| 6 |  | Neutral Base Lacquer |  |
|  | Materials |  | Pounds |
|  | Urethane 60% N.V. |  | 32 |
|  | Long oil alkyd 60% N.V. |  | 352 |
|  | Triton X-45 |  | 7.5 |
|  | Nuxtra ® Calcium 6% |  | 12 |
|  | Bentone Jell 8% |  | 28 |
|  | Disperse the bentone jell under high speed cowles and add: |  |  |
|  | Preparation 2 |  | 16 |
|  | Low odor mineral spirits |  | 85 |
|  | Cyclodex cobalt 6% |  | 3 |
|  | JK 270-70% |  | 76 |
|  | Water |  | 205 |
|  | Anti skin |  | 2 |
|  | Viscosity: | 80-85 KU |  |
|  | W/G: | 7.84 |  |
|  | 60° Gloss: | 85 |  |
|  | SAG: | 6 ml |  |
| 7 |  | O/W Paraffin Wax Emulsion |  |
|  | Part A | 50% Paraffin wax |  |
|  |  | 5% SPAN 60/TWEEN 60 (50/50) (ICI Americas) (sorbitan monostearate/20 dendro sorbitan monostearate) |  |
|  |  | 5% Preparation 2 |  |
|  | Part B | 40% Water |  |

Method of Preparation:
1. Melt Part A ingredients together and heat to 80° C.
2. Heat Part B to 85° C.
3. Add Part B to Part A slowly with moderate agitation until inversion occurs. Add remaining water rapidly.
4. Cool in cold water bath with slow agitation to approximately 35° C.

| Example No. | Filtering Agent | Carrier Ingredients | Composition (% by Wt) |
|---|---|---|---|
| 8 |  | O/W Soft Microcrystalline Wax Emulsion |  |
|  | Part A | 30% Microcrystalline wax |  |

| Example No. | Filtering Agent | Carrier Ingredients | Composition (% by Wt) |
|---|---|---|---|
| | | (Ultraflex Amber Wax-Petrolite Corp.) 30% SPAN ® 60/TWEEN ® 60 (78/22) 5% Preparation 2 | |
| | Part B | 62% Water | |

Method of Preparation:
1. Melt together Part A ingredients and heat to 80–90° C.
2. Heat Part B to boiling.
3. Add Part B to Part A slowly with moderate agitation until inversion occurs. Add remaining water rapidly.
3. Remove from heat and cool to room temperature without stirring.

| Example No. | Filtering Agent | Carrier Ingredients | Composition (% by Wt) |
|---|---|---|---|
| 9 | | O/W Carnauba Wax Emulsion | |
| | Part A | 10% Carnauba wax 3% TWEEN 80 (ICI Americas) (20 dendro sorbitan monooleate) 5% Preparation 2 | |
| | Part B | 82% Water | |

Method of Preparation:
1. Melt Part A ingredients together and heat to 95° C. and hold.
2. Heat Part B to boiling.
3. Add Part B to Part A slowly with moderately fast stirring until inversion occurs. Add remaining water rapidly.
4. Remove emulsion from heat and cool rapidly with stirring.

SUNSCREEN LOTION

Example 10

| PHASE | INGREDIENTS (SUPPLIERS) | PERCENT BY WEIGHT |
|---|---|---|
| A | Petrolatum, Snow White USP (Ruger) | 35.00 |
| | Brij ® 721 (ICI Americas surfactant) | 1.16 |
| | Brij 72 (ICI Americas surfactant) | 3.86 |
| | Silicone Oil, 350 cs (Ruger) | 3.00 |
| | Preparation 1 | 5.00 |
| | Uvinul ® M-40 (BASF) | 3.00 |
| B | Water | 48.08 |
| | Carbopol ® 934 (B. F. Goodrich) | 0.40 |
| C | Sodium Hydroxide (10% Aqueous Solution) | 0.40 |
| D | Dowicil ® 200 (DOW) | 0.10 |

Preparation: Heat (A) to 60° C. Heat (B) to 65° C. Add (B) to (A) slowly with moderate agitation. Add (C). Cool to 50° C. Add (D). Cool, while stirring to 35° C.

SUNSCREEN LOTION

Example 11

| PHASE | INGREDIENTS (SUPPLIERS) | PERCENT BY WEIGHT |
|---|---|---|
| A | Arlamol ® E (ICI Americas, 30 dendro stearyl alcohol | 7.00 |
| | Stearyl Alcohol | 2.50 |
| | Silicone Oil, 350 cs (Ruger) | 5.00 |
| | Arlasolve 200 (ICI) | 2.10 |
| | Brij 72 (ICI) | 4.90 |
| | Preparation No 1 | 5.00 |
| | Preparation No 2 | 3.00 |
| B | Water | 70.00 |
| | Carbopol 934 (B. F. Goodrich) | 0.20 |
| C | Sodium Hydroxide (10% Aqueous Solution) | 0.20 |
| D | Dowicil 200 (DOW) | 0.10 |

Preparation: Heat (A) to 65° C. Heat (B) to 70° C. Add (B) to (A) slowly with moderate agitation. Add (C). Cool to 50° C. Add (D). Cool, while stirring to 35° C.

SUNSCREEN LOTION

Example 12

| PHASE | INGREDIENTS (SUPPLIERS) | PERCENT BY WEIGHT |
|---|---|---|
| A | Arlamol E (ICI) | 7.00 |
| | Stearyl Alcohol | 2.50 |
| | Silicone Oil, 350 cs (Rugher) | 5.00 |
| | Arlasolve ® 200 (ICI 20 dendro isohexadecyl alcohol) | 2.10 |
| | Brij 72 (ICI) | 4.90 |
| | Preparation 1 | 8.00 |
| B | Water | 70.00 |
| | Carbopol ® 934 (B. F. Goodrich) | 0.20 |
| C | Sodium Hydroxide (10% Aqueous Solution) | 0.20 |
| D | Dowicil 200 (DOW) | 0.10 |

Preparation: Heat (A) to 60° C. Heat (B) to 65° C. Add (B) to (A) slowly with moderate agitation. Add (C). Cool to 50° C. Add (D). Cool, while stirring to 35° C.

SUNSCREEN LOTION

Example 13

| PHASE | INGREDIENTS (SUPPLIERS) | PERCENT BY WEIGHT |
|---|---|---|
| A | Petrolatum, Snow White USP (Ruger) | 35.00 |
| | Brij 721 (ICI) | 1.16 |
| | Brij 72 (ICI) | 3.86 |
| | Preparation 3 | 8.00 |
| | Silicone Oil, 350 cs (Ruger) | 3.00 |
| B | Water | 48.08 |
| | Carbopol 934 (B. F. Goodrich) | 0.40 |
| C | Sodium Hydroxide (10% Aqueous Solution) | 0.40 |
| D | Dowicil 200 (DOW) | 0.10 |

Preparation: Heat (A) to 60° C. Heat (B) to 65° C. Add (B) to (A) slowly with moderate agitation. Add (C). Cool to 50° C. Add (D). Cool, while stirring to 35° C.

SUNSCREEN LOTION

Example 14

| PHASE | INGREDIENTS (SUPPLIERS) | PERCENT BY WEIGHT |
|---|---|---|
| A | Arlamol E (ICI) | 7.00 |
|  | Stearyl Alcohol | 2.50 |
|  | Silicone Oil, 350 cs (Ruger) | 5.00 |
|  | Arlasolve ® 200 (ICI) | 2.10 |
|  | Brij 72 (ICI) | 4.90 |
|  | Preparation 4 | 5.50 |
| B | Water | 72.50 |
|  | Carbopol 934 (B. F. Goodrich) | 0.20 |
| C | Sodium Hydroxide (10% Aqueous Solution) | 0.20 |
| D | Dowicil 200 (DOW) | 0.10 |

Preparation: Heat (A) to 65° C. Heat (B) to 70° C. Add (B) to (A) slowly with moderate agitation. Add (C). Cool to 50° C. Add (D). Cool, while stirring to 35° C.

What is claimed is:

1. A compound of the general formula I:

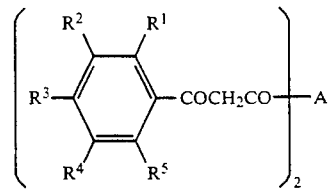

wherein $R^1$–$R^5$ are independently selected from H, both linear and branched alkyl groups having 1 to 10 carbon atoms, —$OR^6$ where $R^6$ is an alkyl group having from 1–10 carbon atoms, and wherein —A— is selected from the group consisting of bivalent (1,2), (1,3), (1,4) cyclohexylene radicals having the formula:

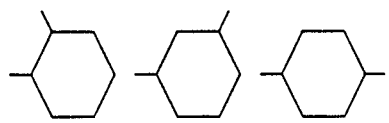

2. A compound of claim 1 wherein $R^1$–$R^5$ are hydrogen and —A— is 1,4-cyclohexylene.

3. A compound of claim 1 wherein $R^1$, $R^2$, $R^4$, $R^5$ are hydrogen, $R^3$ is methoxy and A is 1,4-cyclohexylene.

4. A compound of claim 1 wherein $R^1$–$R^5$ are hydrogen and A is 1,3-cyclohexylene.

5. A compound of claim 1 wherein $R^1$, $R^2$, $R^4$, $R^5$ are hydrogen, $R^3$ is methoxy and A is 1,3-cyclohexylene.

* * * * *